United States Patent
Wick et al.

(10) Patent No.: US 8,779,216 B2
(45) Date of Patent: Jul. 15, 2014

(54) METHOD FOR PRODUCING GUERBET ALCOHOLS

(75) Inventors: Anja Wick, Hilden (DE); Eike Ulf Mahnke, Velbert (DE)

(73) Assignee: Cognis IP Management GmbH, Duesseldorf (DE)

( * ) Notice: Subject to any disclaimer, the term of this patent is extended or adjusted under 35 U.S.C. 154(b) by 248 days.

(21) Appl. No.: 13/508,103

(22) PCT Filed: Oct. 28, 2010

(86) PCT No.: PCT/EP2010/006609
§ 371 (c)(1),
(2), (4) Date: May 4, 2012

(87) PCT Pub. No.: WO2011/054483
PCT Pub. Date: May 12, 2011

(65) Prior Publication Data
US 2012/0220806 A1  Aug. 30, 2012

(30) Foreign Application Priority Data

Nov. 6, 2009 (EP) .................................... 090113922

(51) Int. Cl.
*C07C 29/34* (2006.01)
*C07C 31/125* (2006.01)

(52) U.S. Cl.
CPC ............... *C07C 29/34* (2013.01); *C07C 31/125* (2013.01)
USPC .......................... 568/902.2; 568/881; 568/903

(58) Field of Classification Search
CPC ............................... C07C 29/34; C07C 31/125
USPC ...................... 568/902.2, 881, 903
See application file for complete search history.

(56) References Cited

U.S. PATENT DOCUMENTS

| | | | |
|---|---|---|---|
| 3,119,880 A | 1/1964 | Kollar, John et al. |
| 3,514,493 A | 5/1970 | Pregaglia et al. |
| 3,979,466 A | 9/1976 | Yates |
| 2010/0298613 A1 | 11/2010 | Tanaka et al. |

FOREIGN PATENT DOCUMENTS

| | | |
|---|---|---|
| WO | WO-91/04242 | 4/1991 |
| WO | WO-2009/081727 | 7/2009 |

OTHER PUBLICATIONS

"International Search Report of PCT/EP2010/006609", mailed on Feb. 10, 2011, 3 pages.
Burk, Patrick L. et al., "The Rhodium-Promoted Guerbet Reaction Part I. Higher Alcohols From Lower Alcohols", *Journal of Molecular Catalysis*, 33 1985, pp. 1-14.
Burk, Patrick L. et al., "The Rhodium-Promoted Guerbet Reaction Part II. Secondary Alcohols and Methanol as Substrates", *Journal of Molecular Catalysis*, 33 1985, pp. 15-21.
Carlini, Carlo et al., "Selective synthesis of 2-ethyl-1-hexanol from n-butanol through the Guerbet reaction by usin bifunctional catalysts based on copper or palladium precursors and sodium butoxide", *Journal of Molecular Catalysis A: Chemical 212* 2004, pp. 65-70.
Matsu-Ura, Toyomi et al., "Guerbet Reaction of Primary Alcohols Leading to β-Alkylated Dimer Alcohols Catalyzed by Iridium Complexes", *Journal of Organic Chemistry*, 71 2006, pp. 8306-8308.
O'Lenick, Anthony J. et al., "Guerbet Chemistry", *Journal of Surfacants and Detergents*, vol. 4, No. 3 2001, pp. 311-315.

*Primary Examiner* — Elvis O Price
(74) *Attorney, Agent, or Firm* — Serville Whitney, LLC

(57) ABSTRACT

The invention relates to a method for the dimerization of alcohols in the context of a Guerbet reaction, in which one or more alcohols (A) having 2 to 72 C atoms and 1 to 3 OH groups per molecule are reacted in the presence of (a) a base (B), (b) a carbonyl compound (C), and (c) a hydrogenation catalyst (H) from the group of metals ruthenium, rhodium, palladium, osmium, iridium, and platinum, said metals being in the elementary form, with the proviso that the alcohols (A) have at least one primary or secondary OH group, and that a C atom that carries at least one H atom as a substituent is directly adjacent to the C atom with said primary or secondary OH group.

16 Claims, No Drawings

METHOD FOR PRODUCING GUERBET ALCOHOLS

CROSS-REFERENCE TO RELATED APPLICATIONS

This application is the national stage entry of PCT/EP2010/006609, filed on Oct. 28, 2010, which claims priority to European Patent Application No. EP 09013922.1, filed on Nov. 6, 2009, both of which are incorporated herein by reference in their entireties.

FIELD

The invention relates to a process for producing Guerbet alcohols.

BACKGROUND

Fusel oils are a mixture of middle and higher alcohols (fusel alcohols), fatty acid esters, terpenes and furfurals. They form in the course of alcoholic fermentation as by-products of yeast metabolism, and serve as flavor and aroma carriers in beer, wine and spirits. Examples of fusel alcohols are propanols, butanols, pentanols (e.g. isoamyl alcohol) and hexanols. 3-Methyl-1-butanol (an isoamyl alcohol) is the main constituent of fusel oil. 3-Methyl-1-butanol cannot only be obtained from fusel oil, but also, for example, by hydroformylation and reduction of butane isomers.

Guerbet alcohols are specific branched alcohols. They are primary alcohols branched in the beta position to the $CH_2OH$ group. Guerbet alcohols are known to those skilled in the art, and some have long been commercially available. They are obtained by what is called the Guerbet reaction, a dimerization reaction which has been known for more than 100 years and can be described by the following formula scheme (R* therein is an aliphatic group):

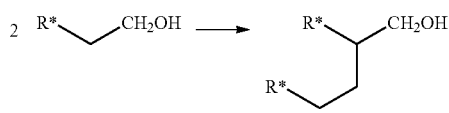

In the conventional Guerbet reaction, a primary or secondary alcohol is converted to a primary alcohol of about twice the molecular weight, which is alkylated in the beta position to the carbon atom bearing the OH group. For instance, n-butanol is converted to 2-ethyl-hexan-1-ol, hexan-1-ol to 2-butyloctan-1-ol and octan-1-ol to 2-hexyldodecan-1-ol.

The primary or secondary alcohols used for the Guerbet reaction bear at least one hydrogen atom on the carbon atom immediately adjacent to the carbon atom with the OH group; in many cases, they bear two hydrogen atoms, which means that the carbon atom with the OH group is directly adjacent to a methylene group.

The condensation product formed can react further with starting alcohol still present in the reaction mixture, which gives rise to a series of further alcohols with higher molecular weight. The extent to which these side reactions proceed depends in the individual case on the nature of the starting alcohols and the reaction conditions. In addition, it is possible for further side reactions to proceed, which lead to aldehydes, ketones, carboxylic acid or carboxylic esters as by-products. U.S. Pat. No. 3,979,466 states, in this regard (cf. column 1 lines 32-35 therein): "It is further indicated that a plurality of different reactions are likely involved so that the process is highly sensitive and unpredictable as to the effect of particular steps".

The Guerbet reaction typically proceeds in the presence of a base at elevated temperature with elimination of water and is one way of converting linear alcohols to branched alcohols. Typically, only a single alcohol is used in the Guerbet reaction. However, it is also possible to use two different alcohols; in this case, reference is made to a mixed Guerbet reaction. The first reaction of the type mentioned in history was published by Marcel Guerbet as early as 1899; he had dimerized n-butanol to 2-ethylhexan-1-ol.

Anthony J. O'Lenick states, in Journal of Surfactants and Detergents, Vol. 4 (2001), p. 311-315, that several component steps proceed in the course of the overall reaction, specifically (a) oxidation of the starting alcohol to the aldehyde, (b) aldol condensation, (c) dehydration (water elimination) to give an unsaturated aldehyde and (d) hydrogenation of the allylic aldehyde.

According to O'Lenick, the following information about the component steps is known: (1) The reaction can in principle proceed without catalyst, but is strongly accelerated by the presence of a hydrogen transfer catalyst. (2) At "relatively low" temperatures (130 to 140° C.), the oxidation process, i.e. the intermediate aldehyde formation, is the rate-determining step. (3) At somewhat higher temperatures (160 to 180° C.), the aldol condensation is the rate-determining step. (4) At even higher temperatures, side reactions become dominant.

Since as early as the 1960s and 1970s, the Guerbet reactions for preparation of commercial products have typically been performed using basic catalysts, generally sodium hydroxide or potassium hydroxide. Frequently, in the Guerbet reaction, as well as the base, an additional catalyst is used, in practice usually zinc oxide.

According to U.S. Pat. No. 3,119,880, alkali metal hydroxides, lead acetate and nickel on kieselguhr can be used, in which case nickel serves as a dehydrogenation catalyst.

According to U.S. Pat. No. 3,979,466, alkali catalysts are used in combination with palladium(II) catalysts.

WO 91/04242 describes an improved Guerbet process in which alcohols are dimerized in the presence of a base and of a carbonyl compound at temperatures above 180° C. The starter alcohols used are alcohols having 4 to 22 carbon atoms, preference being given to alcohols having 6 to 18 carbon atoms. The description also mentions, on p. 9, the option of additionally using a cocatalyst, for example complexes or salts of Al, Ni, B, Mg, Cu, Zn, Ti, Zr or a noble metal of group VIII, especially Pt, Pd, Rh, Ir and Ru, without exemplifying this in the examples.

Carlini et al. describe, in Journal of Molecular Catalysis A (2004), p. 65-70, the preparation of 2-ethylhexanol from butanol by Guerbet reaction of bifunctional catalysts based on Cu or Pd and sodium butoxide. For the very specific case of a reaction of methanol with n-propanol to give i-butanol, they first of all mention the use of a Pd/C catalyst in combination with sodium butoxide at temperatures above 200° C. (page 66, left-hand column, at the bottom). On pages 67-69, they then report on their studies of the self-condensation of butanol at 200° C. under Pd(II) and Pd(0) catalysis in combination with sodium butoxide catalysis. The reactions were performed in a 300 ml reactor, using an amount of about 0.5 mol of butanol. Table 1 on p. 68 summarizes the experimental data. Carlini also studied the extent to which the catalyst used remained "stable" under the reaction conditions. He found that there were "solid deposition and leaching effects", i.e. that the heterogeneous catalyst partly precipitated on the reactor walls and partly went into solution. The leaching of the heterogeneous catalyst used was found to be considerable. Carlini found that 50% of the palladium catalyst used went into solution (cf. p. 69, left-hand column, first paragraph). Carlini arrives at the following conclusion: "This high leaching extent clearly reduces the interest for industrial application perspectives of heterogeneous palladium-based systems". Carlini's conclusion means that he advises the person skilled in the art, at least for industrial applications, against using palladium-based catalyst systems in Guerbet reactions because, as a result of the leaching, there is an exceptionally high loss of the active substance of the catalyst here.

Matsu-ura et al. describe, in Journal of Organic Chemistry (2006), p. 8306-8308, the Guerbet reaction under iridium catalysis in the presence of alkenes and bases. In the paragraph bridging the two columns of p. 8307, it is stated that, under these conditions, 3-methyl-1-butanol (an isoamyl alcohol) can be dimerized in 50% yield (cf. entry 9 of table 2, p. 8307, right-hand column). The dimerization product has the structure:

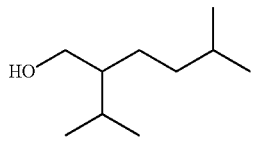

An inconvenient and thus disadvantageous feature of the process according to Matsu-ura is the need to work in the presence of an alkene which serves as a hydrogen acceptor. The iridium-containing catalysts used were [IrCl(cod)]$_2$ or [Cp*IrCl$_2$]$_2$.

WO 2009/081727 A1 describes the dimerization of alcohols having a maximum of 4 carbon atoms. The Guerbet reaction here is performed in the presence of complexes of transition metals and a base. The partial hydrogen pressure here is at least 0.1 MPa.

SUMMARY

Aspects of the invention relate to a process for dimerizing alcohols in the manner of a Guerbet reaction. The method comprises converting one or more alcohols (A) having 2 to 72 carbon atoms and 1 to 3 OH groups per molecule in the presence of a base (B), a carbonyl compound (C) and a hydrogenation catalyst (H) comprising a metal selected from the group consisting of ruthenium, rhodium, palladium, osmium, iridium and platinum, wherein the metal is present in elemental form, wherein the one or more alcohols (A) have at least one primary or secondary OH group and a carbon atom bearing at least one hydrogen atom as a substituent is directly adjacent to the carbon atom having this primary or secondary OH group.

DETAILED DESCRIPTION

Aspects of the invention provide an improved process for dimerizing alcohols in the manner of a Guerbet reaction. This Guerbet reaction should proceed with good yields and with low by-product formation. The process conditions should be at least equivalent compared to the prior art, but if anything be more favorable; this means, more particularly, that the Guerbet reaction should proceed under comparatively favorable temperature and pressure conditions. In addition, catalysts used should be usable in a very resource-protective manner, which means that catalyst losses should be within industrially acceptable limits.

Accordingly, one aspect of the present invention relates to a process for dimerizing alcohols in the manner of a Guerbet reaction, in which one or more alcohols (A) having 2 to 72 carbon atoms and 1 to 3 OH groups per molecule are converted in the presence of (a) a base (B),
(b) a carbonyl compound (C) and
(c) a hydrogenation catalyst (H) from the group of the metals ruthenium, rhodium, palladium, osmium, iridium and platinum, where these metals must be present in elemental form, with the proviso that the alcohols (A) have at least one primary or secondary OH group and a carbon atom bearing at least one hydrogen atom as a substituent is directly adjacent to the carbon atom having this primary or secondary OH group.

In the Guerbet reaction, a single starting alcohol can be used, but it is also possible to use several different alcohols as starting alcohols. The main products formed in the Guerbet reaction are dimerization products, but minor amounts of higher homologs are also formed, especially trimerization products, which result from reaction of the primary dimerization products with as yet unconverted starting alcohols (MA), likewise in the manner of a Guerbet reaction.

If, therefore, a "process for dimerizing alcohols in the manner of a Guerbet reaction" is mentioned, this also includes, as well as the formation of dimerization products, the formation of higher homologs.

If exclusively a primary or secondary monoalcohol of the formula (MA) is used, this is the "conventional" form of the Guerbet reaction; if several primary and/or secondary monoalcohols of the formula (MA) are used, this is a "mixed" Guerbet reaction.

The Starting Alcohols (A)

As stated, the abovementioned compounds (A) are used as starting alcohols for the process according to the invention, namely alcohols which have 2 to 72 carbon atoms and 1 to 3. OH groups per molecule.

In one embodiment, diols are used as starting alcohols. Examples of suitable diols are alpha, omega-diols, vicinal diols and dimer diols.

Dimer diols are compounds which have long been known and are commercially available, which are obtained, for example, by reduction of dimer fatty acids and esters thereof. These are in turn obtained by dimerization of unsaturated carboxylic acids or carboxylic esters, generally fatty acids such as oleic acid, linoleic acid, erucic acid and the like, or esters thereof. Typically, the oligomerization is effected at elevated temperature in the presence of a catalyst composed of alumina, for instance. The substances obtained—dimer fatty acids of technical grade quality—are mixtures wherein the dimerization products predominate. However, small proportions of higher oligomers, especially the trimer fatty acids, are also present. Dimer fatty acids are commercial products and are supplied in various compositions and qualities. In the context of the present invention, preference is given to those dimer diols having a dimer content of at least 70% and especially of at least 90%, and in which the number of carbon atoms per dimer molecule is predominantly in the range from 36 to 44.

In a preferred embodiment, the alcohols (A) are selected from the group of the primary and/or secondary monoalcohols of the formula (MA)

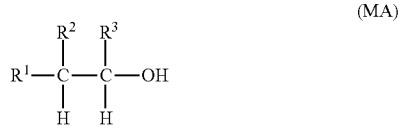

(MA)

where: (a) the total number of carbon atoms of the compounds (MA) is in the range from 2 to 24; (b) the $R^1$, $R^2$ and $R^3$ radicals are each hydrogen or alkyl groups which may each independently be linear or branched or alicyclic, and saturated or unsaturated; (c) the $R^1$ and $R^2$ and/or $R^1$ and $R^3$ and/or $R^2$ and $R^3$ radicals may be joined to one another, i.e. be part of an alicyclic substructure.

The alkyl groups are preferably exclusively saturated.

In the case of the compounds (MA) whose alkyl radicals are exclusively saturated, in a preferred embodiment, the total number of carbon atoms therein is in the range from 4 to 18 and especially in the range from 5 to 10. Particular preference is given to alcohols having 5 carbon atoms and especially isomer mixtures of alcohols having 5 carbon atoms.

3-Methylbutan-1-ol is very particularly preferred as the monoalcohol (MA). It can be used in pure form or in the form of technical mixtures, and also in a blend with other alcohols of the formula (MA), as the starting alcohol.

Examples of suitable compounds (A) having two or more OH groups per molecule are dimer alcohols.

Examples of suitable compounds (MA) are:
 a) primary alcohols, e.g. ethanol, propan-1-ol, butan-1-ol, hexan-1-ol, heptan-1-ol, octan-1-ol, nonan-1-ol, decan-1-ol, undecan-1-ol, dodecan-1-ol, tridecan-1-ol, tetradecan-1-ol, 2-methylbutan-1-ol, 3-methylbutan-1-ol; hexadecan-1-ol, octadecan-1-ol;
 b) secondary alcohols, e.g. propan-2-ol, butan-2-ol, cyclobutanol, pentan-2-ol, pentan-3-ol, cyclopentanol, hexan-2-ol, hexan-3-ol, cyclohexanol, cycloheptanol, cyclooctanol, cyclododecanol.

The compounds (MA) can be used in pure form or in the form of technical products. For the Guerbet reaction to be performed in accordance with the invention, it is also possible to use mixtures which comprise essentially one or more compounds (MA) as well as further substances; one example thereof is the use of fusel oils. Preferably, however, when fusel oils are chosen as the raw material basis, they are purified prior to use in a Guerbet reaction to remove terpenes, furfurals and further accompanying substances, which can be effected, for example, by distillative processes. In one embodiment, accordingly, fusel alcohols or mixtures of fusel alcohols are used as compounds (MA).

The Bases (B)

The selection of the bases (B) for use in the process according to the invention is not critical per se.

Examples of suitable bases (B) are alkali metal and alkaline earth metal hydroxides, alkali metal and alkaline earth metal carbonates, alkoxides, amides and hydrides. Preference is given to using alkali metal hydroxides, especially potassium hydroxide.

In a particularly preferred embodiment, the bases (B) used are those in which potassium functions as the cation. Examples are potassium alkoxides and potassium hydroxide. Potassium hydroxide is very particularly preferred, especially in the form of an aqueous solution, for example as 50% aqueous KOH.

The compounds (B) are preferably used in an amount of 0.5 to 12% by weight, preferably 1.5 to 7% by weight, based on the starting alcohols used.

The method of addition of the base (B) is not critical per se, and it can be added in various ways which can be optimized routinely to the individual case by the person skilled in the art. In one embodiment, the total amount of base (B) is added right at the start of the Guerbet reaction. Especially in the case of short-chain alcohols, it may be more favorable to add the base (B), especially KOH, in portions. Preferably, in the case of metered addition of the base (B) in portions—especially KOH—the Guerbet reaction is run with a pressure ramp known to those skilled in the art, in order to keep the reaction mixture close to the boiling point at constant temperature. The described variants of the metered addition of the base (B) in portions and the use of a pressure ramp usually lead to a significant increase in yield.

The Carbonyl Compounds (C)

The selection of the carbonyl compounds (C) for use in the process according to the invention is not critical per se.

If primary starting alcohols (MA) are used, the carbonyl compounds (C) used are preferably aldehydes, especially those which derive from the starting alcohols (MA) used in that the alcohol group is formally replaced by an aldehyde group.

If secondary starting alcohols (MA) are used, the carbonyl compounds (C) used are preferably ketones, especially those which derive from the starting alcohols (MA) used in that the alcohol group is formally replaced by a keto group.

Preference is given to using the compounds (C) in an amount of 0.01 to 10% by weight, preferably 0.5 to 5% by weight, based on the starting alcohols used.

The Hydrogenation Catalysts (H)

The hydrogenation catalysts (H) to be used are selected from the group of the metals ruthenium, rhodium, palladium, osmium, iridium and platinum, where these metals must be present in elemental form. The expression "in elemental form" is understood to mean that the metals are present in the form of the elements of the zero oxidation state, specifically in the form of the pure metals, and not in the form of compounds or complexes of the metals. This clearly implies that salts or complexes or compounds of these metals are not covered by the definition of the hydrogenation catalysts (H) according to the present invention. Logically, metal-ligand complexes or metal compounds are also not covered by the definition of the hydrogenation catalysts (H) according to the present invention when the metal therein has the zero oxidation state.

The metals mentioned are noble metals of group VIII of the periodic table. They must be present in elemental form and are thus heterogeneous catalysts. Therefore, salts of these metals or complexes of these metals are not covered by the definition of component (H) according to the present invention, nor are complexes of these metals in which the metal is in the zero oxidation state.

In a preferred embodiment, the metals ruthenium, rhodium, palladium, osmium, iridium and platinum are bound into a hydrophobic environment. This can be achieved, for instance, by immobilization of these metals on carbon or on modified silica or hydrophobized silica. The immobilization and hydrophobization can also be effected on other modified mineral framework substances such as zeolites, hydrotalcites or silicates. The fact that the metals are bound into a hydrophobic environment, more particularly are applied to hydrophobic supports, has the advantage that they are substantially protected from being leached out by water and from deactivation by alkaline compounds. Especially when the reaction temperature is below 200° C. and especially below 190° C., a possible leaching effect, which of course means loss of expensive catalyst and is therefore uneconomic in process technology terms, is at an acceptably low level for an industrial process in this manner.

Palladium on carbon (Pd/C) is very particularly preferred as a hydrogenation catalyst (H).

Preference is given to using the catalyst (C) in an amount of 0.0005 to 0.1% by weight, preferably 0.001 to 0.008% by weight, metal content of the catalyst (C) based on the starting alcohols used.

Process Parameters

The optimal reaction temperature for preparation of Guerbet alcohols should be set relatively high according to the prior art; typical working temperatures are in the range from 230-280° C. and especially 245-280° C. In the case of preparation of short-chain Guerbet alcohols having fewer than 16 carbon atoms in particular, vapor pressures of more than 10 bar are attained within this temperature range, which make very high technical demands on the plants and are therefore difficult to achieve. In comparison, the catalyst system for use in accordance with the invention has the advantage that it permits working under milder reaction conditions: for instance, it is possible in the process according to the invention to work at 120-250° C. depending on the starting alcohol used. Preference is given to working at 140 to 230° C. This lowering of the reaction temperature also gives lower pressures, which enable industrial achievement even of short-chain Guerbet alcohols in customary technical plants ($p_{max}$=6 bar). Preference is given to working at pressures of 0.01 to 15 bar and especially 0.1 to 6 bar.

Overall, the process according to the invention is notable for several advantages:

The Guerbet reaction proceeds with good yields.
By-product formation is low.
The reaction temperatures and pressures are lower compared to the prior art.
The hydrogenation catalyst (H) is particularly well protected from leaching by water and from alkaline compounds when the elemental metals (ruthenium, rhodium, palladium, osmium, iridium, platinum) are bound into a hydrophobic environment.
The reaction proceeds under comparatively favorable temperature and pressure conditions.

EXAMPLES

Materials Used

Pd/C: 5% Pd/C 3610 from Johnson Matthey in 50% $H_2O$

Mixed C16-20 Guerbet Alcohol from Octanol/Decanol

Comparative Example 1

A reaction mixture of 2540 g of a mixture of octan-1-ol and decan-1-ol, 70 g of KOH (50%) and 75 g of a mixture of octanal and decanal were heated to 235° C. while stirring under slightly elevated pressure, and stirred at this temperature for 4 hours. The water formed in the reaction was removed. After cooling of the reaction mixture, a reaction mixture containing 64% Guerbet alcohols was obtained.

Example 1a

A reaction mixture of 2540 g of a mixture of octan-1-ol and decan-1-ol, 70 g of KOH (50%) and 75 g of a mixture of octanal and decanal, and 5 g of Pd/C were heated to 225° C. while stirring under slightly elevated pressure, and stirred at this temperature for 2 hours. The water formed in the reaction was removed. After cooling of the reaction mixture, a reaction mixture containing 70% Guerbet alcohols was obtained.

Example 1b

A reaction mixture of 2540 g of a mixture of octan-1-ol. and decan-1-ol, 70 g of KOH (50%) and 75 g of a mixture of octanal and decanal, and 5 g of Pd/C were heated, to 200° C. while stirring under slightly elevated pressure, and stirred at this temperature for 4 hours. The water formed in the reaction was removed. After cooling of the reaction mixture, a reaction mixture containing 64% Guerbet alcohols was obtained.

C10 Guerbet Alcohol (Propylheptanol) From Pentan-1-ol

Comparative Example 2

A reaction mixture of 3100 g of pentan-1-ol and 92 g of pentanal, and also 56 g of KOH (50%), was heated to 220° C. and run at an autogenous pressure of 7 bar with stirring for 22 hours. After cooling, a Guerbet alcohol content of 30% was found.

Example 2

A reaction mixture of 3100 g of pentan-1-ol and 92 g of pentanal, also 56 g of KOH (50%) and 5 g of Pd/C, was heated to 195° C. and run at an autogenous pressure of 5.5 bar with stirring for 5 hours. After cooling, a Guerbet alcohol content of 30% was found.

C10 Guerbet Alcohol From Isoamyl Alcohol

Example 3

A reaction mixture of 2500 g of 3-methyl-1-butanol, 75 g of 3-methyl-1-butanal, 4 g of Pd/C was heated to 180° C., 320 g of KOH (50%) were metered in in portions and the reaction was run with a pressure ramp from 4.6 to 1.4 bar with stirring for 18 hours. After cooling, a Guerbet alcohol content of 75% was found. C12 Guerbet Alcohol from Hexan-1-ol Example 4

A reaction mixture of 2500 g of hexan-1-ol, 75 g of hexanal, 4 g of Pd/C was heated to 210° C., 80 g of KOH (50%) were metered in in portions, and the reaction was run with a pressure ramp from 5 to 3 bar with stirring for 6 hours. After cooling, a Guerbet alcohol content of 38% was found.

The invention claimed is:

1. A process for dimerizing alcohols in the manner of a Guerbet reaction, the process comprising converting one or more alcohols (A) having 2 to 72 carbon atoms and 1 to 3 OH groups per molecule in the presence of
a base (B),
a carbonyl compound (C) and a hydrogenation catalyst (H) comprising a metal selected from the group consisting of ruthenium, rhodium, palladium, osmium, iridium and platinum, wherein the metal is present in elemental form,
wherein the one or more alcohols (A) have at least one primary or secondary OH group and a carbon atom bearing at least one hydrogen atom as a substituent is directly adjacent to the carbon atom having this primary or secondary OH group.

2. The process of claim 1, wherein the one or more alcohols (A) are selected from the group consisting of the primary and/or secondary monoalcohols of the formula (MA)

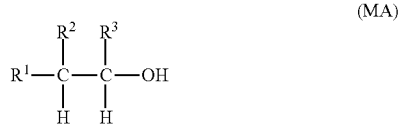

(MA)

where: (a) the total number of carbon atoms of the compounds (MA) is in the range from 2 to 24; (b) the $R^1$, $R^2$ and $R^3$ radicals are each hydrogen or alkyl groups which may each independently be linear or branched or alicyclic, and saturated or unsaturated; (c) the $R^1$ and $R^2$ and/or $R^1$ and $R^3$ and/or $R^2$ and $R^3$ radicals may be joined to one another.

3. The process of claim 2, wherein the alkyl groups are exclusively saturated.

4. The process of claim 3, wherein the total number of carbon atoms in the primary and/or secondary monoalcohols of the formula (MA) is in the range of 4 to 18.

5. The process of claim 4, wherein the total number of carbon atoms in the primary and/or secondary monoalcohols of the formula (MA) is in the range of 5 to 10.

6. The process of claim 5, wherein the monoalcohol (MA) comprises 3-methylbutan-1-ol.

7. The process of claim 1 wherein the base (B) used is a compound selected from the group consisting of the alkali metal and alkaline earth metal hydroxides, alkali metal and alkaline earth metal carbonates, alkoxides, amides and hydrides.

8. The process of claim 1, wherein the base (B) comprises a compound in which potassium functions as a cation.

9. The process of claim 8, wherein the base (B) comprises potassium hydroxide.

10. The process of claim 1, wherein primary starting alcohols (MA) are used, and the carbonyl compounds (C) used are aldehydes which derive from the starting alcohols (MA) used in that the alcohol group is formally replaced by an aldehyde group.

11. The process of claim 1, wherein the metal of the hydrogenation catalyst (H) is embedded in a hydrophobic environment.

12. The process of claim 1, wherein the hydrogenation catalyst (H) comprises palladium on carbon (Pd/C).

13. The process of claim 1, wherein the conversion reaction is performed within the temperature range of 140° C. to 230° C.

14. The process of claim 1, wherein the conversion reaction is performed at a pressure in the range of 0.1 to 6 bar.

15. The process of claim 2, wherein $R^1$ and $R^2$ and/or $R^1$ and $R^3$ and/or $R^2$ and $R^3$ radicals are joined to one another to form an alicyclic substructure.

16. The process of claim 1, wherein the secondary starting alcohols (MA) are used, and the carbonyl compounds (C) used are ketones which derive from the starting alcohols (MA) used in that the alcohol group is formally replaced by a keto group.

* * * * *

UNITED STATES PATENT AND TRADEMARK OFFICE
CERTIFICATE OF CORRECTION

PATENT NO. : 8,779,216 B2  
APPLICATION NO. : 13/508103  
DATED : July 15, 2014  
INVENTOR(S) : Anja Wick et al.

Page 1 of 1

It is certified that error appears in the above-identified patent and that said Letters Patent is hereby corrected as shown below:

On the Title Page of the patent, please correct the following:

"(74) Attorney, Agent, or Firm — Serville Whitney, LLC" should be changed to --(74) Attorney, Agent, or Firm — Servilla Whitney LLC--.

Signed and Sealed this
Twenty-eighth Day of October, 2014

Michelle K. Lee
*Deputy Director of the United States Patent and Trademark Office*